United States Patent

[19]

Förster

[11] 4,264,769
[45] Apr. 28, 1981

[54] PROCESS FOR THE PREPARATION OF HYDROXYPHENYL ETHERS

[75] Inventor: Heinz Förster, Wuppertal-Elberfeld, Fed. Rep. of Germany

[73] Assignee: Bayer Aktiengesellschaft, Leverkusen, Fed. Rep. of Germany

[21] Appl. No.: 8,821

[22] Filed: Feb. 2, 1979

[30] Foreign Application Priority Data

Feb. 13, 1978 [DE] Fed. Rep. of Germany ....... 2805983

[51] Int. Cl.³ ................. C07D 237/14; C07D 239/34; C07D 277/68; C07C 41/04
[52] U.S. Cl. .................................. 544/239; 544/241; 544/336; 546/290; 546/297; 548/165; 548/173; 568/585; 568/637; 568/638; 260/465 F
[58] Field of Search ............... 568/635, 637, 639, 586, 568/638; 260/304 B, 465 F; 548/165; 544/239, 241, 336; 546/290, 297

[56] References Cited

U.S. PATENT DOCUMENTS

| | | | |
|---|---|---|---|
| 1,744,961 | 1/1930 | Hale ..................... | 568/635 |
| 2,905,672 | 9/1959 | Steck ..................... | 544/241 |
| 2,950,325 | 8/1960 | Brittan et al. ............ | 568/637 |
| 3,220,979 | 11/1965 | McNelis ................... | 568/637 |
| 3,532,759 | 10/1970 | Schnell et al. ............ | 568/637 |
| 3,652,257 | 3/1972 | Jojima .................... | 544/241 |
| 3,755,467 | 8/1973 | Darsow et al. ............. | 568/639 |
| 3,966,453 | 6/1976 | Takahashi et al. .......... | 568/637 |
| 3,966,826 | 6/1976 | Trosken ................... | 568/637 |
| 4,133,675 | 1/1979 | Schurter et al. ........... | 546/297 |

FOREIGN PATENT DOCUMENTS

| | | | |
|---|---|---|---|
| 206444 | 11/1959 | Austria ................... | 544/241 |
| 2005883 | 9/1970 | Fed. Rep. of Germany ...... | 548/637 |
| 2847662 | 5/1979 | Fed. Rep. of Germany ...... | 568/637 |

*Primary Examiner*—Anton H. Sutto
*Assistant Examiner*—D. B. Springer
*Attorney, Agent, or Firm*—Sprung, Felfe, Horn, Lynch & Kramer

[57] ABSTRACT

A novel process for the preparation of a hydroxyphenyl ether compound of the formula

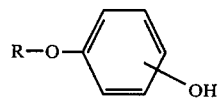

(I), in which R represents a radical of the formula

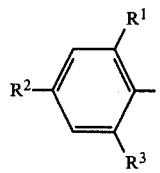

wherein
$R^1$, $R^2$ and $R^3$ are independently selected from hydrogen, halogen, haloalkyl, nitro or cyano; or
R represents a heterocyclic radical which optionally carries one or more substituents selected from halogen, halogenoalkyl, alkoxy, nitro and cyano and which can contain an optionally substituted fused benzene ring, which process comprises reacting a halogen compound of the formula

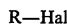

R—Hal  (II)

in which
R is defined as above, and
Hal is fluorine, chlorine or bromine,
with a dihydroxybenzene of the formula

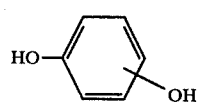

(III)

in the presence of calcium hydroxide and in the presence of a polar diluent, at a temperature of from 20° C. to 200° C.

19 Claims, No Drawings

PROCESS FOR THE PREPARATION OF HYDROXYPHENYL ETHERS

The present invention relates to a process for the preparation of hydroxyphenyl ether compounds. These materials are useful as intermediates for the synthesis of herbicidally active compounds.

It is known that nitrohydroxydiphenyl ethers can be prepared by reacting p-nitrochlorobenzene with alkali metal salts of dihydroxybenzenes, from German Offenlegungsschrift (German Published Specification) 2,157,781. However, this process has a number of disadvantages. Thus, it is limited to the preparation of diphenyl ethers. Furthermore, it is not uniformly suitable for reaction of the various dihydroxybenzenes. Whereas from the alkali metal salts of para-dihydroxybenzenes, such as hydroquinone, and p-nitrochlorobenzene the corresponding nitrohydroxydiphenyl ethers are formed in very good yields, if meta-dihydroxy compounds, for example, are used as starting materials and the process is carried out in an analogous manner, the desired products are obtained in only moderate yields of lower quality, which can be attributed, inter alia, to the formation of bis-ethers.

Furthermore, it is known that 1,3-bis-(2,6-dichloro-4-trifluoromethyl-phenoxy)-benzene is obtained by reacting 2 moles of 3,4,5-trichlorobenzotrifluoride with 1 mole of the potassium salt of resorcinol, from DT-OS (German Published Specification) No. 2,311,628. Attempts to synthesize 2,6-dichloro-4-trifluoromethyl-3'-hydroxy-diphenyl ether by an analogous method give only unsatisfactory results. On the other hand, on carrying out the reaction at about 140° C., a product which contains many compounds is obtained, from which the desired 2,6-dichloro-4-trifluoromethyl-3'-hydroxydiphenyl ehter can be isolated only with great difficulty and in a low amount. On the other hand, on carrying out the reaction at a temperature of about 160° C., a considerable amount of 1,3-bis-(2,6-dichloro-4-trifluoromethyl-phenoxy)benzene is formed.

The present invention now provides a process for the preparation of hydroxyphenyl ethers of the general formula

in which R represents a radical of the formula

wherein

R$^1$, R$^2$ and R$^3$, independently of one another, each represent hydrogen, halogen, halogenoalkyl, nitro or cyano, or R represents a heterocyclic radical which optionally carries one or more substituents selected independently from halogen, halogenoalkyl, alkoxy, nitro and cyano and which can contain an optionally substituted fused benzene ring, in which a halogen compound of the general formula

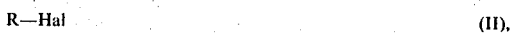

wherein

R has the meaning stated above and

Hal represents fluorine, chlorine or bromine (especially chlorine or bromine), is reacted with a dihydroxybenzene of the general formula

in the presence of calcium hydroxide and in the presence of a polar diluent, at temperatures between 20° C. and 200° C.

Preferably R represents a radical of the formula

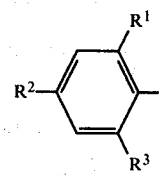

in which

R$^1$, R$^2$ and R$^3$, which need not be identical, each represent hydrogen, chlorine, trifluoromethyl, nitro or cyano, provided that at least one of the radicals R$^1$, R$^2$ and R$^3$ represents trifluoromethyl, nitro or cyano and that at least one of the radicals R$^1$, R$^2$ and R$^3$ represents chlorine or R represents a 5-membered or 6-membered heterocyclic radical, which is optionally substituted by chlorine and/or nitro and/or cyano, containing 1 to 3 heteroatoms in the ring selected independently from nitrogen, sulphur and oxygen atoms, and which can also be fused with a benzene ring which optionally carries one or more substituents selected from chlorine, trifluoromethyl, methoxy and ethoxy.

Preferred heterocyclic radicals R are those of the general formulae

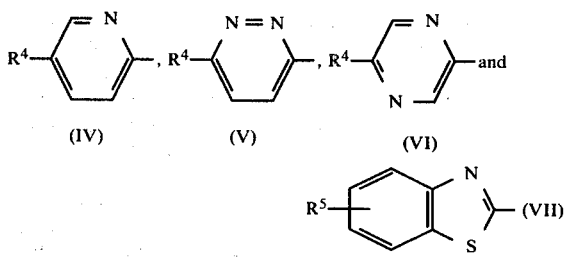

in which in each of the formulae (IV) to (VI), R$^4$ represents hydrogen, chlorine, nitro or cyano, and in the formula (VII), R$^5$ represents hydrogen, chlorine, trifluoromethyl, methoxy or ethoxy.

It is to be described as exceptionally surprising that hydroxyphenyl ethers of the formula (I) are accessible in high yield and excellent purity by the process according to the invention, since it was to be expected, with regard to the known state of the art, that the same complications would occur in the process as in the analogous reaction of p-nitrochlorobenzene with dihydroxybenzenes in the presence of alkali metal hydroxides. In particular, it was in no way to be predicted that the formation of undesired bisethers can be substantially suppressed by replacing alkali metal hydroxides by the base calcium hydroxide, which is scarcely used in organic chemistry.

The process according to the invention has a number of advantages. Thus, it is not restricted to the synthesis of diphenyl ethers, but has a relatively broad application.

Quite apart from this advantage, it can also be carried out on an industrial scale in a relatively simple manner. As already mentioned, in the process according to the invention, the hydroxyphenyl ethers can be obtained in high yield and excellent purity and almost free from troublesome by-products. An additional advantage is that working up presents no problems. After diluting and acidifying the reaction mixture, the products are usually obtained in the crystalline form and can be filtered off without difficulty. Moreover, the calcium hydroxide employed as the base is a particularly inexpensive industrial product. The process according to the invention thus represents a valuable enrichment of the art.

If 3,4,5-trichloro-benzotrifluoride and resorcinol are used as starting compounds, the course of the reaction can be represented by the equation which follows:

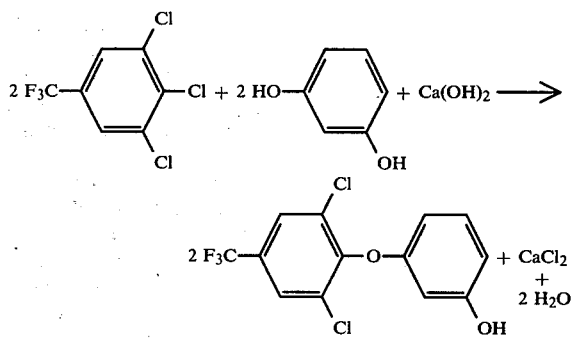

The starting materials of the formula (II) which can be used according to the invention are already known, or they can be prepared by known processes. Examples which may be mentioned are: 1-chloro-2-trifluoromethyl-, 1-chloro-4-trifluoromethyl-, 1-chloro-2-nitro-, 1-chloro-4-nitro-, 1-chloro-2-cyano-, 1-chloro-4-cyano-, 1,2-dichloro-4-trifluoromethyl-, 1,4-dichloro-2-trifluoromethyl-, 1,2-dichloro-4-nitro-, 1,4-dichloro-2-nitro-, 1,2-dichloro-4-cyano-, 1,4-dichloro-2-cyano-, 1,2,3-trichloro-5-trifluoromethyl-, 1,2,3-trichloro-5-nitro-, 1,2,3-trichloro-5-cyano-, 1-chloro-2,4-bistrifluoromethyl-, 1-chloro-2,4-dinitro-, 1-chloro-2,4-dicyano-, 1-chloro-2-trifluoromethyl-4-nitro, 1-chloro-4-trifluoromethyl-2-nitro-, 1-chloro-2-trifluoromethyl-4-cyano-, 1-chloro-4-trifluoromethyl-2-cyano-, 1-chloro-2-nitro-4-cyano and 1-chloro-4-nitro-2-cyano-benzene; 2-chloro-, 2,5-dichloro-, 2-chloro-5-nitro- and 2-chloro-5-cyanopyridine; 2-chloro-, 2,5-dichloro-, 2-chloro-5-nitro- and 2-chloro-5-cyano-pyridazine; 2-chloro-, 2,5-dichloro-, 2-chloro-5-nitro- and 2-chloro-5-cyano-pyrazine; and 2-chloro-, 2,4-, 2,5-, 2,6- and 2,7-dichloro-, 4-, 5-, 6- and 7-trifluoromethyl-2-chloro-, 4-, 5-, 6- and 7-methoxy-2-chloro- and 4-, 5-, 6- and 7-ethoxy-2-chloro-benzthiazole.

The preferred dihydroxybenzenes of the formula (III), also required as starting materials, are resorcinol and hydroquinone.

Calcium hydroxide is used as the base in the process according to the invention.

Possible diluents which can be employed in carrying out the process according to the invention are all the polar aprotic solvents, preferably nitriles, such as acetonitrile and propionitrile, amides, such as dimethylformamide, dimethylacetamide and hexamethylphosphoric acid triamide, and nitromethane, dimethylsulphoxide, tetramethylene sulphone and N-methylpyrrolidone.

The reaction temperatures can be varied within a relatively wide range. In general, the reaction is carried out at temperatures of from 20° C. to 200° C., preferably from 50° C. to 140° C.

The pressure is not critical in carrying out the process according to the invention. In general, the reaction is carried out under normal pressure. However, it is also possible to carry out the reaction under a slightly increased or reduced pressure, for example between 0.5 and 5 bars.

In carrying out the process according to the invention, in general up to 2.5 moles, preferably 1.2 to 2.0 moles, of dihydroxybenzene of the formula (III) and 0.8 to 1.5 moles, preferably 1.0 to 1.2 moles, of calcium hydroxide are employed per mole of halogen compound of the formula (II).

In general, the process according to the invention is carried out by a procedure in which the dihydroxybenzene of the formula (III) is initially introduced, dispersed in the solvent, together with the calcium hydroxide, and the halogen compound of the formula (II) is then added as a solid or in solution, the reaction temperature already being appropriately adjusted before adding the compound of the formula (II). However, it is also possible to dissolve all the reactants in the solvent at room temperature, that is to say between 10° C. and 30° C., and then to bring the complete mixture to the reaction temperature.

The mixture is worked up by customary methods. In general, a procedure is followed in which, after the reaction has ended, the reaction mixture is poured into water and acifified with hydrochloric acid or sulphuric acid and the product is separated off. After the acidification, the reaction products are as a rule obtained as crystals and can be filtered.

The hydroxyphenyl ethers of the formula (I) which can be prepared by the process according to the invention are valuable starting materials for the synthesis of aryloxycarboxylic acid derivatives, which possess outstanding herbicidal properties (see Belgian Patent Specification No. 853,574).

Thus, for example, 3-(2-nitro-4-trifluoromethylphenoxy)-α-phenoxypropionic acid methyl ester of the formula

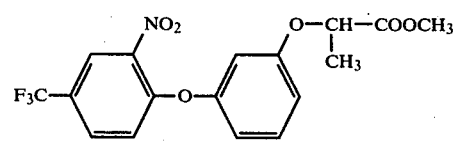

can be prepared by reacting 2-nitro-4-trifluoromethyl-3′-hydroxy-diphenyl ether with α-bromopropionic acid methyl ester in the presence of methanol and sodium methylate, or in the presence of acetonitrile and potassium carbonate. This synthesis can be represented by means of an equation as follows:

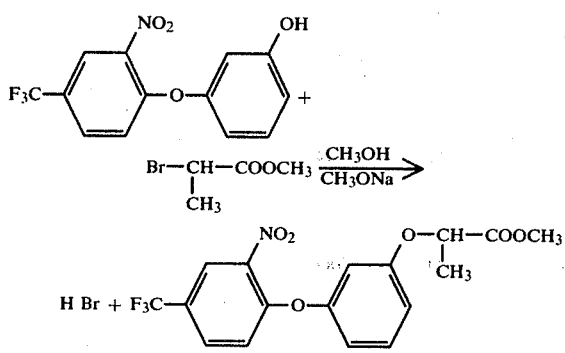

The process according to the invention is illustrated by the examples which follow:

EXAMPLE 1

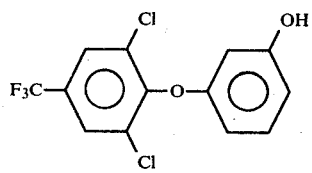 (1)

(a) Preparation by the process according to the invention 358 g (1.5 mol) of 3,4,5-trichlorobenzotrifluoride were added dropwise to a mixture of 330 g (3 mol) of resorcinol and 111 g (1.5 mol) of calcium hydroxide in 2 liters of dimethylsulfoxide at 120°–130° C. in the course of 7 hours. Thereafter, the reaction mixture was stirred at 130° C. for 8 hours. After cooling to room temperature, the reaction mixture was poured into 7 liters of water, whereupon the reaction product separated out as an oil. The mixture was extracted with 3 liters of toluene and the organic phase was separated off and, after drying, was concentrated. The residue was distilled. 350 g (73% of theory) of 2,6-dichloro-4-trifluoromethyl-3'-hydroxydiphenyl ether were obtained in this manner in the form of a solid product of melting point 64°–65° C. Boiing point 123°–130° C./0.15 mm Hg Analysis: Empirical formula: $C_{13}H_7Cl_2F_3O_2$: Calculated: 48.3% C; 2.2% H; 22.0% Cl. Found: 48.3% C; 2.3% H; 21.8% Cl.

(b) Preparation by a known process, using sodium hydroxide as the base 358 g (1.5 mol) of 3,4,5-trichloro-benzotrifluoride were added dropwise to a mixture of 330 g (3 mol) of resorcinol and 60 g (1.5 mol) of sodium hydroxide in 2 liters of dimethylsulphoxide at 120°–130° C. in the course of 7 hours. Thereafter, the reaction mixture was stirred at 130° C. for 8 hours. After cooling to room temperature, the reaction mixture was stirred into a solution of 80 g of sodium hydroxide in 7 liters of water. The insoluble portion was separated off and taken up in toluene; according to the thin layer chromatogram, this solution contained no 2,6-dichloro-4-trifluoromethyl-3'-hydroxydiphenyl ether. In order to work up the aqueous phase, it was acidified with hydrochloric acid and the oil which separated out was extracted with toluene. After drying, the solvent was stripped off and the residue was distilled. 30 g (6.7% of theory) of 2,6-dichloro-4-trifluoromethyl-3'-hydroxydiphenyl ether were obtained in this manner. Boiling point 123°–130° C./0.15 mm Hg.

EXAMPLE 2

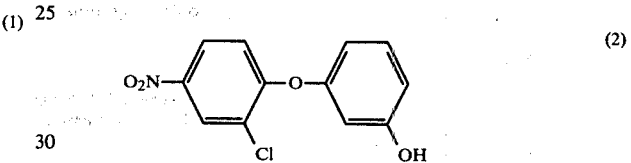 (2)

A solution of 192 g (1 mol) of 1,2-dichloro-4-nitrobenzene in 300 ml of dimethylsulphoxide was added to a mixture of 220 g (2 mol) of resorcinol, 74 g (1 mol) of calcium hydroxide and 1 liter of dimethylsulphoxide, while stirring. The mixture was warmed to 80°–85° C. for 5 hours, while stirring. Thereafter, the reaction mixture was cooled to room temperature and poured into aqueous hydrochloric acid, whereupon the product precipitated as crystals. After filtering off, 220.6 g (83% of theory) of 3-hydroxy-2'-chloro-4'-nitro-diphenyl ether were obtained in the form of yellow crystals of melting point 94°–95° C.

The compounds of the general formula

 (I)

listed in Table 1 below were prepared in the same manner.

| Example No. | R | Position of the OH group | Product | Yield (% of theory) | Melting point(°C.) |
|---|---|---|---|---|---|
| 3 | O₂N—⌬— | 3 | 1-Hydroxy-3-(4-nitro-phenoxy)-benzene | 70 | 93 |
| 4 | O₂N—⌬—CN | 3 | 1-Hydroxy-3-(2-cyano-4-nitro-phenoxy)-benzene | 71 | 145 |

-continued

| Example No. | R | Position of the OH group | Product | Yield (% of theory) | Melting point(°C.) |
|---|---|---|---|---|---|
| 5 | F₃C—⌬—NO₂ | 3 | 1-Hydroxy-3-(2-nitro-4-trifluoromethyl-phenoxy)-benzene | 79 | (oil) |
| 6 | O₂N—⌬N— | 3 | 1-Hydroxy-3-(5-nitro-pyridin-2-yl-oxy)-benzene | 85 | 114 |
| 7 | Cl—⌬N=N— | 3 | 1-Hydroxy-3-(6-chloro-pyridazin-3-yl-oxy)-benzene | 71 | 189 |
| 8 | N⌬N— | 3 | 1-Hydroxy-3-(pyrazin-2-yl-oxy)-benzene | 72 | 101 |
| 9 | ⌬N⟩—S | 3 | 1-Hydroxy-3-(benzthiazol-2-yl-oxy)-benzene | 71 | 146 |
| 10 | ⌬N⟩—S | 4 | 1-Hydroxy-4-(benzthiazol-2-yl-oxy)-benzene | 81 | 169 |
| 11 | O₂N—⌬— | 4 | 1-Hydroxy-4-(4-nitrophenoxy)-benzene | 98 | 171 |
| 12 | O₂N—⌬—Cl | 4 | 1-Hydroxy-4-(2-chloro-4-nitrophenoxy)-benzene | 98 | 149 |
| 13 | CF₃—⌬(Cl)(Cl)— | 4 | 1-Hydroxy-4-(2,6-dichloro-4-trifluoromethyl-phenoxy)-benzene | 78 | 136 |

Preparation of 3-(2-nitro-4-trifluoromethylphenoxy)-α-phenoxy-propionic acid methyl ester starting from 2-nitro-4-trifluoromethyl-3'-hydroxy-diphenyl ether

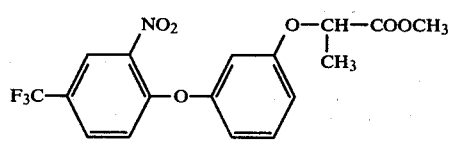

17 g (0.057 mol) of 2-nitro-4-trifluoromethyl-3'-hydroxy-diphenyl ether and 9.1 g of potassium carbonate were boiled under reflux in 80 ml of acetonitrile for 1 hour. 11.4 g of 2-bromopropionic acid methyl ester were then added dropwise at 50°–55° C. in the course of 1 hour and the mixture was subsequently stirred at 50°–55° C. for a further 6 hours.

For working up, the reaction mixture was poured into 300 ml of water and extracted with 500 ml of toluene. The toluene was then distilled off in vacuo. 18.5 g (84.3% of theory) of 3-(2-nitro-4-trifluoromethylphenoxy)-phenoxypropionic acid methyl ester were obtained in this manner in the form of a yellowish oil.

Analysis: Empirical formula: $C_{17}H_{14}F_3NO_6$: Calculated: 53% C; 3.6% H; 3.6% N. 52.8% C; 3.5% H; 3.5% N.

It will be understood that the specification and examples are illustrative but not limitative of the present invention and that other embodiments within the spirit and scope of the invention will suggest themselves to those skilled in the art.

What is claimed is:

1. In a process for the preparation of hydroxyphenyl ether compound of the formula

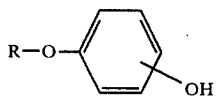

in which R represents a radical of the formula

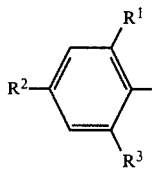

wherein
 $R^1$ is hydrogen, chlorine, nitro or cyano,
 $R^2$ is trifluoromethyl or nitro, and
 $R^3$ is hydrogen or chlorine, provided that one of $R^1$ and $R^3$ is chlorine; or
 R represents a heterocyclic radical selected from those of the formulae

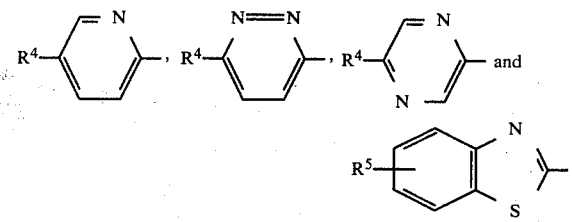

in which
 $R^4$ represents hydrogen, chlorine, nitro or cyano and
 $R^5$ represents hydrogen, chlorine, trifluoromethyl, methoxy or ethoxy
the improvement which is reacting a halogen compound of the formula R—Hal  (II)

in which
 R is defined as above, and
 Hal is fluorine, chlorine or bromine,
with a dihydroxybenzene of the formula

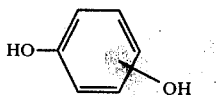

in the presence of 0.8 to 1.5 moles calcium hydroxide per mole of halogen compound (II) and in the presence of an organic aprotic polar diluent, at a temperature of from 20° C. to 200° C.

2. Process as claimed in claim 1 wherein R is a radical of the formula

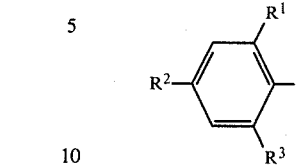

3. Process as claimed in claim 2 wherein $R^2$ is trifluoromethyl.

4. Process as claimed in claim 2 wherein at least one of $R^1$ and $R^2$ is nitro.

5. Process as claimed in claim 2 wherein $R^1$ is cyano.

6. Process as claimed in claim 1 wherein the reaction is carried out at a temperature from 50° to 140° C.

7. Process as claimed in claim 1 wherein said polar diluent is selected from acetonitrile, propionitrile, dimethylformamide, dimethylacetamide, hexamethylphosphoric acid triamide, nitromethane, dimethylsulphoxide, tetramethylene sulphone or N-methylpyrrolidone.

8. Process as claimed in claim 1 wherein 2.5 moles of the dihydroxybenzene compound, compound (III) are used per mole of halogen compound (II).

9. Process as claimed in claim 1 wherein 1.2 to 2.0 moles of dihydroxybenzene (III) and 1.0 to 1.2 moles of calcium hydroxide are employed per mole of halogen compound (II).

10. Process as claimed in claim 1 wherein Hal is chlorine or bromine.

11. Process as claimed in claim 1 wherein compound (III) is resorcinol or hydroquinone.

12. Process as claimed in claim 1 wherein 2,6-dichloro-4-trifluoromethyl-3'-hydroxy-diphenyl ether is prepared by reacting 3,4,5-trichloro-benzotrifluoride with resorcinol.

13. Process as claimed in claim 1 wherein 3-hydroxy-2'-chloro-4'-nitro-diphenyl ether is prepared by reacting 1,2-dichloro-4-nitro-benzene with resorcinol.

14. Process as claimed in claim 1 wherein 1-hydroxy-3-(2-nitro-4-trifluoromethyl-phenoxy)-benzene is prepared.

15. Process as claimed in claim 1 wherein 1-hydroxy-3-(benzthiazol-2-yl-oxy)-benzene is prepared.

16. Process as claimed in claim 1 wherein 1-hydroxy-4-(2,6-dichloro-4-trifluoromethyl-phenoxy)-benzene is prepared.

17. Process as claimed in claim 1 wherein said polar diluent is selected from nitriles and amides.

18. Process as claimed in claim 1 wherein up to about 2.5 moles of dihydroxybenzene compound (III) are used per mole of halogen compound (II).

19. Process as claimed in claim 1 wherein approximately equal molar quantities of calcium hydroxide and halogen compound (II) are used.

* * * * *